United States Patent
Jerussi (12)

(10) Patent No.: US 6,333,345 B1
(45) Date of Patent: Dec. 25, 2001

(54) METHODS OF USING AND COMPOSITIONS COMPRISING N-DESMETHYLZOLPIDEM

(75) Inventor: Thomas P. Jerussi, Framingham, MA (US)

(73) Assignee: Sepracor, Inc., Marlborough, MA (US)

( * ) Notice: Subject to any disclaimer, the term of this patent is extended or adjusted under 35 U.S.C. 154(b) by 0 days.

(21) Appl. No.: 09/563,858

(22) Filed: May 4, 2000

Related U.S. Application Data

(60) Provisional application No. 60/134,238, filed on May 14, 1999.

(51) Int. Cl.$^7$ .................................................. A61K 31/415
(52) U.S. Cl. ............................................ 514/399; 514/400
(58) Field of Search ...................................... 514/399, 400

(56) References Cited

U.S. PATENT DOCUMENTS

| | | | |
|---|---|---|---|
| 4,382,938 | 5/1983 | Kaplan et al. | 424/256 |
| 4,382,983 | * 5/1983 | Kaplan et al. | 424/256 |
| 4,794,185 | * 12/1988 | Rossey et al. | 546/121 |

FOREIGN PATENT DOCUMENTS

| | | |
|---|---|---|
| 1076089 | 7/1967 | (GB) . |
| 96/31210 | 10/1996 | (WO) . |

OTHER PUBLICATIONS

Buhr, A. and Siegel, E., *Proc. Natl. Acad. Sci. USA* 94(16):8824–8829 (1997).

Castello, R.A. and Mattocks, A.M., *J. Parm. Sci.* 51(2):106–108 (1962).

Criswell, H.E., et al., *Neuropharmacology* 36(11–12):1641–1652 (1997).

Depoortere, H. et al., *J. Pharmacol. Exp. Ther.* 237(2):649–658 (1986).

Goodman & Gilman's *The Pharmacological Basis of Therapeutics*, Hardman, J.G., et al., eds., 372, 365–372 (9$^{th}$ ed., 1996).

*Handbook of Pharmaceutical Excipients*, 2$^{nd}$ ed., Wade and Willer eds., pp. 257–259 (1994).

*Physicians' Desk Reference*, 2929–2933 (53$^{rd}$ ed. 1999).

*Remingtons: The Practice of The Science and Pharmacy*, 19$^{th}$ ed., Gennaro, ed., p. 1625 (1995).

Scatton, B., et al., *J. Pharmacol. Exp. Ther.* 237(2):659–665 (1986).

Villikka, K., et al., *Clin. Pharmacol. Ther.* 62(6):629–634 (1997).

\* cited by examiner

*Primary Examiner*—Dwayne C. Jones
(74) *Attorney, Agent, or Firm*—Pennie & Edmonds LLP

(57) ABSTRACT

The invention is directed to compositions comprising, and methods of using, N-desmethylzolpidem in the treatment and prevention of diseases and conditions in mammals. Examples of such diseases and conditions include, but are not limited to: sleep disorders such as insomnia; affective disorders such as depression, attention deficit disorder, and attention deficit disorder with hyperactivity or attention deficit/hyperactivity disorder; convulsive disorders such as epilepsy; anxiety; aggressive behavior; spasticity or acute muscle spasm; behavioral disorders; schizophrenia; and disorders associated with abnormal plasma hormone levels such as endocrine disorders.

31 Claims, No Drawings

METHODS OF USING AND COMPOSITIONS COMPRISING N-DESMETHYLZOLPIDEM

This application claims priority to U.S. provisional patent application No. 60/134,238, filed May 14, 1999.

1. FIELD OF THE INVENTION

The invention relates to compositions and methods for the treatment and prevention of sleep, convulsive, and related disorders.

2. BACKGROUND OF THE INVENTION

Zolpidem, chemically named N,N,6-trimethyl-2-p-tolyl-imidazo[1,2-a]pyridine-3-acetamide, is a non-benzodiazepine hypnotic which has the following structure:

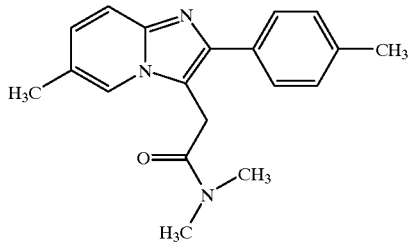

A 2:1 tartrate complex of zolpidem is sold under the tradename AMBIEN® and is indicated for the short-term treatment of insomnia. *Physicians' Desk Reference*, 2929–2933 (53$^{rd}$ ed. 1999). The synthesis of zolpidem is described by U.S. Pat. Nos. 4,382,938 and 4,794,185.

Zolpidem binds at or near benzodiazepine receptors, particularly those found within GABA$_A$ receptor chloride channel macromolecular complexes located in the central nervous system. Scatton, B., et al., *J. Pharmacol. Exp. Ther.* 237(2):659–665 (1986); Criswell, H. E., et al., *Neuropharmacology* 36(11–12):1641–1652 (1997); Buhr, A. and Sigel, E., *Proc Natl. Acad Sci USA* 94(16):8824–8829 (1997). At least three subtypes of benzodiazepine, or omega (ω), receptors are believed to exist within GABA$_A$ receptor complexes, but zolpidem preferentially binds in vitro to the ω$_1$ receptor. *Physicians' Desk Reference*, 2929 (53$^{rd}$ ed. 1999). The sedative, anticonvulsant, anxiolytic, and myorelaxant properties of zolpidem are believed to be due to its ability to allosterically modulate the activity of GABA$_A$ complexes by increasing trans-membrane conductance of chloride ions. This stabilizes neuronal membrane potentials and dampens excitatory input. Id.; *Goodman & Gilman's The Pharmacological Basis of Therapeutics*, Hardman, J. G., et al., eds., 365–372 (9$^{th}$ ed., 1996).

Zolpidem is chemically unrelated to the benzodiazepines but possesses a similar spectrum of activity. Id.; Depoortere, H. et al., *J. Pharmacol. Exp. Ther.* 237(2):649–658 (1985). In addition to the treatment of insomnia, zolpidem has been claimed to be useful in the treatment of other conditions such as convulsions (U.S. Pat. No. 4,382,938), migraine headaches (U.S. Pat. No. 5,767,117), and parkinsonian and related extrapyramidal symptoms (WO 96/31210).

Zolpidem is readily absorbed through the gastrointestinal tract, and is reportedly eliminated almost entirely in the liver largely by oxidation of the methyl groups on the phenyl and imidazopyridine rings to the corresponding carboxylic acids. *Goodman & Gilman's The Pharmacological Basis of Therapeutics*, Hardman, J. G., et al., eds., 372 (9$^{th}$ ed., 1996). Metabolism of zolpidem is primarily attributed to CYP3A4, and it has been found that inducers of CYP3A4 such as rifampicin, phenytoin, and carbamazepine reduce the pharmacodynamics of zolpidem. Villikka, K., et al., *Clin. Pharmacol. Ther.* 62(6):629–634 (1997).

The metabolites of zolpidem are reportedly inactive. See, e.g., *Goodman & Gilman's The Pharmacological Basis of Therapeutics*, Hardman, J. G., et al., eds., 372 (9$^{th}$ ed., 1996); *Physicians' Desk Reference*, 2930 (53$^{rd}$ ed. 1999).

While zolpidem is effective in the treatment of insomnia, unfortunately, there are adverse effects associated with both short term and chronic use of the drug. These include, but are not limited to, headache, dizziness, vertigo, confusion, lack of coordination, lethargy or drowsiness the day after use, and gastrointestinal problems such as nausea and diarrhea.

3. SUMMARY OF THE INVENTION

The invention is directed to compositions comprising, and methods of using, N-desmethylzolpidem in the treatment and prevention of diseases and conditions in mammals.

Zolpidem metabolites are reported to be pharmacologically inactive. According to this invention, however, N-desmethylzolpidem can be used in the treatment or prevention of a disease or condition in a mammal which is affected by the modulation of one or more benzodiazepine receptors. Further, N-desmethylzolpidem can be used in the treatment or prevention of such diseases and conditions while avoiding adverse effects associated with zolpidem. Further still, N-desmethylzolpidem can be adjunctively administered with drugs that affect the activity of the enzyme CYP3A4 to provide pharmacological effects that differ from those of zolpidem when it is adjunctively administered with such drugs.

One embodiment of the invention encompasses a method of treating or preventing a sleep disorder in a patient which comprises administering to a patient in need of such treatment or prevention a therapeutically effective amount of N-desmethylzolpidem or a pharmaceutically acceptable salt, solvate, or clathrate thereof. A particular method of this embodiment is the treatment or prevention of insomnia.

Another embodiment of the invention encompasses a method of treating or preventing an affective disorder in a patient which comprises administering to a patient in need of such treatment or prevention a therapeutically effective amount of N-desmethylzolpidem or a pharmaceutically acceptable salt, solvate, or clathrate thereof. A particular method of this embodiment is the treatment or prevention of depression. Another method of this embodiment is the treatment or prevention of attention deficit disorder or attention deficit disorder with hyperactivity.

Yet another embodiment of the invention encompasses a method of treating or preventing a convulsive state in a patient which comprises administering to a patient in need of such treatment or prevention a therapeutically effective amount of N-desmethylzolpidem or a pharmaceutically acceptable salt, solvate, or clathrate thereof. A particular method of this embodiment is the treatment or prevention of epilepsy or epileptic seizures.

Still another embodiment of the invention encompasses a method of treating or preventing anxiety in a patient which comprises administering to a patient in need of such treatment or prevention a therapeutically effective amount of N-desmethylzolpidem or a pharmaceutically acceptable salt, solvate, or clathrate thereof. A particular method of this embodiment is the treatment or prevention of acute anxiety. Another method of this embodiment is the treatment or prevention of chronic anxiety.

Another embodiment of the invention encompasses a method of treating or preventing aggressive behavior in a patient which comprises administering to a patient in need of such treatment or prevention a therapeutically effective amount of N-desmethylzolpidem or a pharmaceutically acceptable salt, solvate, or clathrate thereof.

Yet another embodiment of the invention encompasses a method of treating or preventing spasticity or acute muscle spasm spasticity in a patient which comprises administering to a patient in need of such treatment or prevention a therapeutically effective amount of N-desmethylzolpidem or a pharmaceutically acceptable salt, solvate, or clathrate thereof.

Still another embodiment of the invention encompasses a method of treating or preventing a behavioral disorder in a patient which comprises administering to a patient in need of such treatment or prevention a therapeutically effective amount of N-desmethylzolpidem or a pharmaceutically acceptable salt, solvate, or clathrate thereof.

Another embodiment of the invention encompasses a method of treating a schizophrenic disorder in a patient which comprises administering to a patient in need of such treatment or prevention a therapeutically effective amount of N-desmethylzolpidem or a pharmaceutically acceptable salt, solvate, or clathrate thereof.

Yet another embodiment of the invention encompasses a method of treating or preventing a disease or condition associated with abnormal plasma hormone levels in a patient which comprises administering to a patient in need of such treatment or prevention a therapeutically effective amount of N-desmethylzolpidem or a pharmaceutically acceptable salt, solvate, or clathrate thereof. In a particular method of this embodiment, the disorder is an endocrine disorder.

Patients who may receive the therapeutic or prophylactic benefits of the methods of the invention include those suffering from the diseases or conditions described above, and include, but are not limited to, young patients (e.g., humans less than about 15 years of age), old patients (e.g., humans older than about 60 years of age), patients suffering from renal or liver disease or damage, patients prone to suffer from renal or liver damage such as recovering alcoholics, patients currently being treated with a muscarinic antagonist or a muscarinic agonist, and patients who are susceptible to adverse effects associated with zolpidem.

Another embodiment of the invention encompasses pharmaceutical compositions comprising N-desmethylzolpidem or pharmaceutically acceptable salts, solvates, or clathrates thereof. Typical pharmaceutical compositions of the invention will comprise N-desmethylzolpidem and a pharmaceutically acceptable carrier. Preferred pharmaceutical compositions are lactose free.

Also encompassed by the invention are single unit dosage forms of N-desmethylzolpidem or pharmaceutically acceptable salts, solvates, or clathrates thereof. Single unit dosage forms of the invention are suitable for oral, mucosal (e.g., nasal, vaginal, or rectal), parenteral (e.g., subcutaneous, intravenous, bolus injection, intramuscular, or intraarterial), sublingual, transdermal, or buccal administration. Preferred single unit dosage forms of N-desmethylzolpidem are suitable for oral or parenteral administration. Preferred single unit dosage forms of N-desmethylzolpidem for oral administration are tablets, capsules and caplets.

4. DETAILED DESCRIPTION OF THE INVENTION

The invention relates to the use of N-desmethylzolpidem which, until now, was believed to possess no pharmacological activity. A general aspect of the invention encompasses the use of N-desmethylzolpidem to treat or prevent diseases and conditions which are affected by the modulation of one or more benzodiazepine receptors.

The metabolite, N-desmethylzolpidem, has the following structure:

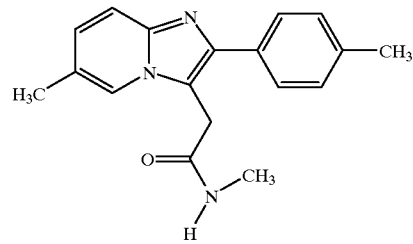

As used herein, the terms "mammal" and "patient" are used interchangeably, and include human.

As used herein, the term "pharmaceutically acceptable salt" refers to salts prepared from pharmaceutically acceptable non-toxic organic or inorganic acids. Examples of suitable non-toxic acids include, but are not limited to, maleic, fumaric, benzoic, ascorbic, embonic, succinic, oxalic, bis-methylenesalicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-aminobenzoic, glutamic, benzene sulfonic and theophylline acetic acids, 8-halotheophyllines such as 8-boromo-theophylline, hydrochloric, hydrobromic, sulfuric, sulfamic, phosphoric, nitric, alginic, anthranilic, camphorsulfonic, ethenesulfonic, formic, furoic, galacturonic, glucuronic, isethionic, maleic, malic, mucic, pamoic, pantothenic, phenylacetic, propionic, sulfanilic, tartaric, p-toluenesulfonic acid. A preferred non-toxic acid is tartaric acid.

As used herein, the term "benzodiazepine receptor agonist" means a compound that mimics the in vitro binding activity of a benzodiazepine (e.g., diazepam) to central or peripheral benzodiazepine receptors. As used herein, a benzodiazepine receptor agonist may exhibit full or partial agonistic effects as defined by *Goodman & Gilman's The Pharmacological Basis of Therapeutics,* Hardman, J. G., et al., eds. p. 364 (9th ed., 1996). Simply because a compound is referred to herein as a "benzodiazepine receptor agonist," however, does not imply that it exhibits a mechanism of action, a site of action, or an induced receptor conformational change identical to that of a benzodiazepine.

As used herein, the terms "diseases and conditions which are affected by the modulation of one or more central or peripheral benzodiazepine receptors," "diseases and conditions which are affected by the modulation of one or more benzodiazepine receptors," and "disease or condition affected by the modulation of a benzodiazepine receptor" mean a disease or condition that has at least one symptom which is mitigated or alleviated by allosteric binding of a compound to benzodiazepine receptors. Preferably, the at least one symptom is mitigated or alleviated by an increase in the trans-neuronal membrane chloride current associated with the binding of only GABA to benzodiazepine receptor complexes. Specific diseases and conditions which are affected by the modulation of one or more benzodiazepine receptors include, but are not limited to: sleep disorders such as insomnia; affective disorders such as depression, attention deficit disorder (ADD), and attention deficit disorder with hyperactivity (ADDH) or attention deficit/hyperactivity disorder (ADHD); convulsive disorders such as epilepsy; anxiety; aggressive behavior; spasticity or acute muscle spasm; behavioral disorders, such as mood anxiety and schizophrenia; and disorders associated with abnormal plasma hormone levels such as endocrine disorders.

As used herein, the terms "treating or preventing sleep disorders" and "treatment and prevention of sleep disorders" mean reducing the severity of symptoms associated with sleep disorders such as insomnia, insomnia of a primary nature with little apparent relationship to immediate somatic or psychic events, and insomnia which is secondary to some acquired pain, anxiety or depression. Symptoms associated with sleep disorders include, but are not limited to, difficulty in sleeping and disturbed sleep patterns.

As used herein, the terms "treating or preventing an affective disorder" and "treatment and prevention of an-affective disorder" mean reducing the severity of symptoms associated with a disorder characterized by abnormality of emotional state, including, but not limited to, depression, dysthymia, attention deficit disorder, attention deficit disorder with hyperactivity, bipolar disorder, bipolar and manic conditions, and the like. The terms "attention deficit disorder" (ADD) and "attention deficit disorder with hyperactivity" (ADDH), or attention deficit/hyperactivity disorder (AD/HD), are used herein in accordance with the accepted meanings as found in the *Diagnostic and Statistical Manual of Mental Disorders*, 4$^{th}$ Ed., American Psychiatric Association (1997) (DSM-IV™).

As used herein, the terms "treating or preventing depression" and "treatment and prevention of depression" mean reducing the severity of symptoms associated with depression which include, but are not limited to, changes in mood, feelings of intense sadness, despair, mental slowing, loss of concentration, pessimistic worry, agitation, and self-deprecation. Symptoms associated with depression may also be physical symptoms, which include, but are not limited to, insomnia, anorexia, weight loss, decreased energy and libido, and abnormal hormonal circadian rhythms.

As used herein, the terms "treating or preventing a convulsive state" and "treatment and prevention of a convulsive state" mean reducing the severity and/or frequency of symptoms associated with convulsive states which include, but are not limited to, recurrent, sudden, and often brief alterations of consciousness, motor activity, sensory phenomena, and autonomic responses which are often characterized by convulsive seizures and/or tonic or clonic jerking of the extremities. The term "convulsive state" encompasses epilepsy and specific types of epileptic seizures including, but not limited to, Tonic-clonic (Grand Mal), Partial (Focal) seizures, psychomotor (Complex partial) seizures, pyknoepileptic or Absence (Petit Mal) seizure, and Myoclonic seizures.

As used herein, the terms "treating or preventing anxiety" and "treatment and prevention of anxiety" mean reducing the severity of symptoms associated with acute and/or chronic anxiety caused by psychologic and/or physiologic factors. Symptoms associated with acute anxiety include, but are not limited to, a fear of losing control of one's own actions, a sense of terror arising from no apparent reason, and a dread of catastrophe. Symptoms associated with chronic anxiety include, but are not limited to, uneasiness, nervousness, nagging uncertainty about future events, headache, fatigue, and subacute autonomic symptoms.

As used herein, the terms "treating or preventing aggressive behavior" and "treatment and prevention of aggressive behavior" mean reducing the frequency and/or severity of manifestations of aggressive behavior which include, but are not limited to, aggressive or socially inappropriate vocal outbursts and acts of physical violence.

As used herein, the terms "treating or preventing spasticity," "treatment and prevention of spasticity," "treating or preventing spasticity and acute muscle spasm," and "treatment and prevention of spasticity and acute muscle spasm" include reducing the severity of symptoms associated with a range of abnormalities of skeletal muscle regulation that result from problems of the nervous system. A predominant symptom is heightened muscle tone or hyperexcitability of tonic stretch muscle reflexes. Symptoms of acute muscle spasm include, but are not limited to, trauma, inflammation, anxiety, and pain.

As used herein, the terms "treating or preventing a behavioral disorder" and "treatment and prevention of a behavioral disorder" mean reducing or relieving the symptoms of a behavioral disorder, such as mood anxiety, which include, but are not limited to, a subjective sense of terror, a dread of catastrophe, uneasiness, nervousness, uncertainty, headache, fatigue, disturbed thinking, inappropriate effect, auditory hallucinations, aggressive outbursts, and the like.

As used herein, the terms "treating or preventing a schizophrenic disorder" and "treatment and prevention of a schizophrenic disorder" mean reducing the severity of symptoms associated with schizophrenic disorders. Symptoms of schizophrenic disorders include, but are not limited to, psychotic symptoms of disturbed thinking, feeling and general behavior. Specific symptoms of schizophrenic disorders include the inability to form clear, goal-directed thought, and emotional changes such as blunting and inappropriate affect. Other symptoms of schizophrenic disorders include auditory hallucinations, delusions of persecution, threats of violence, minor aggressive outbursts, aggressive behavior, disturbances of movement such as significant overactivity and excitement, and retardation and stupor.

As used herein, the terms "treating or preventing a disease associated with abnormal plasma hormone levels" and "treatment and prevention of a disease associated with abnormal plasma hormone levels" mean reducing the symptoms of diseases or conditions related to abnormal plasma levels of hormones including, but not limited to, growth hormone, ACTH, prolactin, luteinizing hormone, and other adrenocortical and testicular hormones. The term "disease associated with abnormal plasma hormone levels" encompasses endocrine disorders such as, but not limited to, growth hormone deficiency, gonadotropin deficiency, Cushing's syndrome, Grave's disease, hypothyroidism, and Addison's disease.

4.1. Synthesis and Preparation

N-desmethylzolpidem is readily prepared by at least two synthetic methods. First, N-desmethylzolpidem may be prepared from zolpidem using an appropriate N-dealkylation reaction. Zolpidem itself can be prepared according to methods well known in the art, including those disclosed by U.S. Pat. Nos. 4,382,938 and 4,794,185, both of which are incorporated herein by reference. Suitable N-dealkylation reaction conditions are well known in the art. See, e.g., March, J., *Advanced Organic Chemistry* 407, 709 (4$^{th}$ ed. 1992).

In a second method, N-desmethylzolpidem is prepared as shown in Scheme I:

Scheme 1

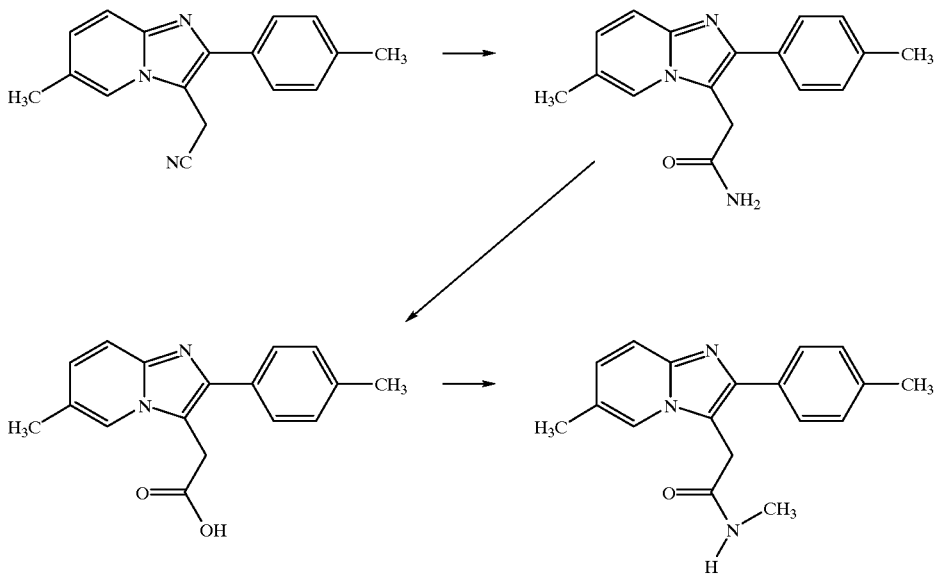

wherein suitable reaction conditions are well known in the art and are also disclosed by U.S. Pat. No. 4,382,938, which is incorporated herein by reference. Preparation of the starting material is described in the literature, and by British Patent No. 1,076,089, which is incorporated herein by reference.

Isolation and purification of N-desmethylzolpidem is preferably done using chromatography, preferably column chromatography, and more preferably high performance liquid chromatography (HPLC). Other methods, such as isolation by evaporation of the solvent, followed by recrystallization, may also be employed.

4.2. Pharmaceutical Compositions and Method of Use

The magnitude of a prophylactic or therapeutic dose of N-desmethylzolpidem in the acute or chronic management of the diseases or conditions recited herein will vary with the nature and severity of the disease or condition. The magnitude of a prophylactic or therapeutic dose will also vary according to the route by which the active ingredient is administered. The dose, and perhaps the dose frequency, will further vary according to the age, body weight, and response of the individual patient. Suitable dosing regimens can be readily selected by those skilled in the art with due consideration of such factors. In general, the recommended daily dose range for the conditions described herein lies within the range of from about 1 mg to about 500 mg per day, given as a single once-a-day dose or as divided doses from 2 to 4 times per day. Preferably, a daily dose range is from about 5 mg to about 250 mg per day, more preferably, from about 10 mg to about 200 mg per day. In managing a patient, the therapy should be initiated at a lower dose, perhaps from about 1 mg to about 10 mg, and increased if necessary up to from about 10 mg to about 200 mg per day as either a single dose or divided doses, depending on the patient's global response.

It may be necessary to use dosages of the active ingredient outside the ranges disclosed herein in some cases, as will be apparent to those of ordinary skill in the art. For example, it is recommended that a daily dose be reduced by at least about 50% in elderly patients. Further, because elimination of N-desmethylzolpidem from the bloodstream is dependant on renal and liver function, it is recommended that the total daily dose be reduced by at least about 75% in patients with moderate hepatic impairment, and that it be reduced by about 50% in patients with mild to moderate renal impairment. It is noted that the clinician or treating physician will know how and when to interrupt, adjust, or terminate therapy in conjunction with individual patient response.

The phrase "therapeutically effective amount," as used herein with respect to the treatment or prevention of diseases and conditions encompasses the above described dosage amounts and dose frequency schedules. Different therapeutically effective amounts may be applicable for different diseases and conditions, as will be readily known by those of ordinary skill in the art. Similarly, amounts sufficient to treat or prevent such disorders, but insufficient to cause adverse effects associated with zolpidem, are also encompassed by the above described dosage amounts and dose frequency schedules.

Any suitable route of administration may be employed for providing the patient with an effective dosage of N-desmethylzolpidem. Suitable routes include, but are not limited to, oral, mucosal (e.g., nasal, vaginal, or rectal), parenteral (e.g., subcutaneous, intravenous, bolus injection, intramuscular, or intraarterial), sublingual, transdermal, and buccal. Preferred routes of administration are oral and parenteral.

The pharmaceutical compositions of the invention comprise N-desmethylzolpidem, or a pharmaceutically acceptable salt, solvate, or clathrate thereof as an active ingredient, and may also contain a pharmaceutically acceptable carrier and optionally other therapeutic ingredients known to those skilled in the art.

Compositions of the invention are suitable for oral, mucosal (e.g., nasal, vaginal, or rectal), parenteral (e.g., subcutaneous, intravenous, bolus injection, intramuscular, or intraarterial), sublingual, transdermal, or buccal administration, although the most suitable route in any given case will depend on the nature and severity of the condition being treated. The compositions may be conveniently presented in unit dosage form and prepared by any of the methods well known in the part of pharmacy. Dosage forms include tablets, caplets, troches, lozenges, dispersions, suspensions, suppositories, solutions, capsules, soft elastic gelatin capsules, patches, and the like. Preferred dosage forms are suitable for oral or parenteral administration.

In practical use, N-desmethylzolpidem can be combined as the active ingredient in intimate admixture with a pharmaceutically acceptable carrier according to conventional pharmaceutical compounding techniques. The carrier may take a wide variety of forms and comprises a number of components depending on the form of preparation desired for administration. The compositions of the invention include, but are not limited to, suspensions, solutions and elixirs; aerosols; or excipients, including, but not limited to, starches, sugars, microcrystalline cellulose, diluents, granulating agents, lubricants, binders, disintegrating agents, and the like. Preferably, the pharmaceutical composition is in the form of an oral or parenteral preparation.

Pharmaceutical compositions of the invention suitable for oral administration may be presented as discrete pharmaceutical unit dosage forms, such as capsules, cachets, soft elastic gelatin capsules, tablets, caplets, or aerosols sprays, each containing a predetermined amount of the active ingredients, as a powder or granules, or as a solution or a suspension in an aqueous liquid, a non-aqueous liquid, an oil-in-water emulsion, or a water-in-oil liquid emulsion. Such compositions may be prepared by any method known in the art of pharmacy which comprises the step of bringing an active ingredient into association with a carrier. In general, the compositions are prepared by uniformly and intimately admixing the active ingredients with liquid carriers or finely divided solid carriers or both, and then, if necessary, shaping the product into the desired presentation. Oral solid preparations are preferred over oral liquid preparations. Preferred oral solid preparations are capsules, tablets, and caplets.

A tablet may be prepared by compression or molding techniques. Compressed tablets may be prepared by compressing in a suitable machine the active ingredient in a free-flowing form, such as powder or granules, optionally mixed with one or more pharmaceutically acceptable excipients, such as a binder, lubricant, inert diluent, granulating agent, surface active or dispersing agent, or the like. Molded tablets may be made by molding, in a suitable machine, a mixture of the powdered compound moistened with an inert liquid diluent. Preferably, each tablet, cachet, caplet, or capsule contains from about 1 mg to 500 mg, more preferably from about 5 mg to about 250 mg, and most preferably from about 10 mg to about 200 mg.

Pharmaceutical compositions of the invention may also be formulated as a pharmaceutical composition in a soft elastic gelatin capsule unit dosage form by using conventional methods well known in the art. See, e.g., Ebert, *Pharm. Tech*, 1(5):44–50 (1977). Soft elastic gelatin capsules have a soft, globular gelatin shell somewhat thicker than that of hard gelatin capsules, wherein a gelatin is plasticized by the addition of plasticizing agent, e.g., glycerin, sorbitol, or a similar polyol. The hardness of the capsule shell may be changed by varying the type of gelatin used and the amounts of plasticizer and water. The soft gelatin shells may contain a preservative, such as methyl- and propylparabens and sorbic acid, to prevent the growth of fungi. The active ingredient may be dissolved or suspended in a liquid vehicle or carrier, such as vegetable or mineral oils, glycols, such as polyethylene glycol and propylene glycol, triglycerides, surfactants, such as polysorbates, or a combination thereof.

A pharmaceutically acceptable excipient used in the compositions and dosage form of the invention may be a binder, a filler, a mixture thereof. A pharmaceutically acceptable excipient may also include a lubricant, a disintegrant, or mixtures thereof. One embodiment of the invention encompasses a pharmaceutical composition which is substantially free of all mono- or di-saccharide excipients. Another embodiment encompasses a pharmaceutical compositions which is free of lactose.

Binders suitable for use in the compositions and dosage forms of the invention include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose or mixtures thereof.

Suitable forms of microcrystalline cellulose include, for example, the materials sold as AVICEL-PH-101, AVICEL-PH-103 and AVICEL-PH-105 (available from FMC Corporation, American Viscose Division, Avicel Sales, Marcus Hook, Pa., U.S.A.). An exemplary suitable binder is a mixture of microcrystalline cellulose and sodium carboxymethyl cellulose sold as AVICEL RC-581 by FMC Corporation.

Fillers suitable for use in the compositions and dosage forms of the invention include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, or mixtures thereof.

The binder/filler in pharmaceutical compositions of the invention is typically present in about 50 to about 99 weight percent of the pharmaceutical composition.

Disintegrants are used to cause the tablet to disintegrate when exposed to an aqueous environment. Too much of a disintegrant will produce tablets which may disintegrate in the bottle due to atmospheric moisture; too little may be insufficient for disintegration to occur and may thus alter the rate and extent of release of the drug ingredient(s) from the dosage form. Thus, a sufficient amount of disintegrant that is neither too little nor too much to detrimentally alter the release of the drug ingredient(s) should be used to form dosage forms of N-desmethylzolpidem made according to the invention. The amount of disintegrant used varies based upon the type of formulation and mode of administration, and is readily discernible to those of ordinary skill in the art. Typically, about 0.5 to about 15 weight percent of disintegrant, preferably about 1 to about 5 weight percent of disintegrant, may be used in the pharmaceutical composition.

Disintegrants suitable for use in the compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants suitable for use in the compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, or mixtures thereof. Additional lubricants include, for example, a syloid silica gel (AEROSIL 200, manufactured by W.R. Grace Co. of Baltimore Md.), a coagulated aerosol of synthetic silica (marketed by Deaussa Co. of Plano, Tex.), CAB-O-SIL (a pyrogenic silicon dioxide product sold by Cabot Co. of Boston, Mass.), or mixtures thereof. A lubricant may optionally be added, typically in an amount of less than about 1 weight percent of the pharmaceutical composition.

In addition to the common dosage forms set out above, the compounds of the invention may also be administered by controlled release means or delivery devices that are well known to those of ordinary skill in the art, such as those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, the disclosures of which are each incorporated herein by express reference thereto. These pharmaceutical compositions can be used to provide slow or controlled-release of one or more of the active ingredients therein using, for example, hydropropylmethyl cellulose, other polymer matrices, gels, permeable membranes, osmotic systems, multilayer coatings, microparticles, liposomes, microspheres, or the like, or a combination thereof to provide the desired release profile in varying proportions. Suitable controlled-release formulations known to those of ordinary skill in the art, including those described herein, may be readily selected for use with the pharmaceutical compositions of the invention. Thus, single unit dosage forms suitable for oral administration, such as tablets, capsules, gelcaps, caplets, and the like, that are adapted for controlled-release are encompassed by the invention.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations may include: 1) extended activity of the drug; 2) reduced dosage frequency; and 3) increased patient compliance. In addition, controlled-release formulations can be used to effect the time of onset of action, or other characteristics, such as blood levels of the drug, and thus may affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

The controlled-release of an active ingredient may be stimulated by various inducers, for example pH, temperature, enzymes, water, or other physiological conditions or compounds. The term "controlled-release component" in the context of the invention is defined herein as a compound or compounds, including, but not limited to, polymers, polymer matrices, gels, permeable membranes, liposomes, microspheres, or the like, or a combination thereof, that facilitates the controlled-release of the active ingredient.

Pharmaceutical compositions of the invention may also be formulated for parenteral administration by injection (e.g., subcutaneous, intravenous, bolus injection, intramuscular, or intraarterial), and may be dispensed in a unit dosage form, such as a multidose container or an ampule. Such compositions for parenteral administration may be in the form of suspensions, solutions, emulsions, or the like in aqueous or oily vehicles, and in addition to the active ingredients may contain one or more formulary agents, such as dispersing agents, suspending agents, stabilizing agents, preservatives, and the like.

The invention is further defined by reference to the following examples describing in detail the preparation of the compositions of the invention. It will be apparent to those skilled in the art that many modifications, both to materials and methods, may be practiced without departing from the purpose and interest of this invention.

5. EXAMPLES

5.1. Example 1: Determination of Biological Activity

A pharmacologic study is conducted to determine the relative potency, comparative efficacy, and binding affinity of N-desmethylzolpidem. The pharmacologic profile of hypnotic-sedative, anxiolytic agents of the benzodiazepine class is well established, and has been extended to non-benzodiazepine agents of the cyclopyrrolone class. See, e.g., *Goodman & Gilman's The Pharmacological Basis of Therapeutics*, Hardman, J. G., et al., eds. ch. 17, pp. 361–396 ($9^{th}$ ed., 1996); Bardone, M. C., et al., Abstract No. 2319, $7^{th}$ *Int. Congr. Pharm. Paris*, (July, 1978: Pergamon Press, London); Julou, L. et al., *Pharmacology, Biochemistry and Behavior*, 23:653–659 (1985).

A variety of experimental models can be used to characterize the various activities of N-desmethylzolpidem, including its anticonvulsant, myorelaxant, anti-aggressive, sedative-hypnotic, and anxiolytic (i.e., anti-anxiety) activities. In an examination of each element of the pharmacologic profile, N-desmethylzolpidem is compared with pharmacologic standards such as nitrazepam and diazepam in a variety of animal models. The dose (mg/kg) of each agent that is capable of inhibiting by 50% (the $ID_{50}$ or $ED_{50}$) an induced response in rodents, for example, provides the basis for comparison. Pentylenetetrazole-induced, picrotoxin convulsions, and electrically-induced convulsions can thus be used to demonstrate the anti-convulsant activity of N-desmethylzolpidem. Haefely, W., *Psychotropic Agents*, Hofmeister, F. and Stille, G., eds., part 11, pp. 12–262 (Springer Verlag, Berlin: 1981). Further, in the rat, in the amygdala kindled model of epilepsy, daily electrical stimulation of the amygdala induces a progressive increase of epileptic afterdischarge duration, with increasing epileptic behavioral symptoms, producing in about two weeks a generalized convulsive crisis. Presumably, previously ineffective stimuli have sensitized neuronal pathways, and it has been suggested that a similar mechanism may exist for the induction of an anxiety state in man after repeated stresses.

Similar models are available for determination of the myorelaxant, anti-aggressive, and sedative-hypnotic activities of N-desmethylzolpidem in both mice and rats. See, Julou, L. et al., *Pharmacology, Biochemistry and Behavior*, 23:653–659 (1985).

The pharmacologic activity of N-desmethylzolpidem may also be compared with benzodiazepines for its affinity for binding to both CNS and peripheral benzodiazepine receptors. In this biochemical affinity binding study, the binding of $^3$H-radiolabeled N-desmethylzolpidem is studied in a synaptosomal membrane preparation of cerebral tissue from female rat brain. The tissue is preferably prepared by homogenization in ice-cold isosmotic (0.32 M) sucrose, and centrifugation, first at low speed (1,000×g for 10 minutes), with the resultant supernatant solution then being centrifuged at high speed (48,000×g for 20 minutes). The resulting pellet is suspended in Kreb-Tris buffer at pH 7.4, and the concentration of protein is adjusted to 15 mg/ml. This synaptosomal membrane preparation may be stored at −18° C. until used at room temperature (e.g., about 22° C.) with the radio-cyclopyrrolone in Kreb-Tris buffer solution pH 7.4. Following a 30-minute incubation, separation of the bound and free drug is preformed by centrifugation at 1,000×g for 10 minutes in scintillation vials. The supernatant solution is collected, the pellet is dissolved in a counting vehicle, and the radioactivity is counted using a liquid scintillation counter. The original supernatant solution from the first incubation, which contains unbound radiolabeled drug, may be used in additional binding studies using the same method. Additional controls involve, for instance, study of the radioactivity bound in the presence of 10 $\mu$M flunitrazepam (a benzodiazepine), which experiment is useful in assessing non-specific binding. Furthermore, the binding of various concentrations of radiolabeled N-desmethylzolpidem in the presence of a fixed concentration of GABA provides additional information-as to the modulation of the GABA-ergic system by N-desmethylzolpidem. See, Jacqmin, P., et al., *Arch. Int. Pharmacodyn.* 282:26–32 (1986); Jacqmin, P., et al, *J. Pharm. Belg.* 40:35–54 (1985). With regard to peripheral benzodiazepine receptors and their distinction from central benzodiazepine binding sites, see, e.g., Verma, A. and Snyder, S. H., *Ann. Rev. Pharmacol. Toxicol.* 29:307–322 (1989), which is hereby incorporated by reference.

5.2. Example 2: Oral Formulation

Suitable ingredients of a tablet dosage form of N-desmethylzolpidem are provided in Table 1.

TABLE 1

| Component | Quantity per Tablet (mg) |
|---|---|
| N-desmethylzolpidem | 75 |
| Lactose | 125 |
| Corn Starch | 5.0 |
| Water (per thousand tablets) | 30.0 ml* |
| Magnesium Stearate | 0.5 |

*The water evaporates during manufacture.

The active ingredient (i.e., N-desmethylzolpidem) is blended with the lactose until a uniform blend is formed. The smaller quantity of corn starch is blended with a suitable quantity of water to form a corn starch paste. This is then mixed with the uniform blend until a uniform wet mass is formed. The remaining corn starch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine using ¼ mesh stainless steel screen. The magnesium stearate is then blended and the resulting mixture is compressed into tablets of desired shape, thickness, hardness and disintegration. Tablets may be coated by standard aqueous or nonaqueous techniques.

Another tablet dosage formulation suitable for use with an active ingredient of the invention is provided by Table 2:

TABLE 2

| | Quantity per Tablet (mg) | | |
|---|---|---|---|
| Component | Formula A | Formula B | Formula C |
| N-desmethylzolpidem | 20 | 40 | 100 |
| Lactose BP | 134.5 | 114.5 | 309.0 |
| Starch BP | 30 | 30 | 60 |
| Pregelatinized Maize Starch BP | 15 | 15 | 30 |
| Magnesium Stearate | 0.5 | 0.5 | 1.0 |
| Compression Weight | 200 | 200 | 500 |

The active ingredient is sieved and blended with lactose, starch, and pregelatinized maize starch. Suitable volumes of purified water are added and the powders are granulated. After drying, the granules are screened and blended with the magnesium stearate. The granules are then compressed into tablets using punches.

Tablets of other strengths may be prepared by altering the ratio of active ingredient to pharmaceutically acceptable carrier, the compression weight, or by using different punches.

5.3. Example 3: Oral Formulation

Capsules of N-desmethylzolpidem may be made using the ingredients provided in Table 3:

TABLE 3

| | Quantity per Capsule (mg) | | |
|---|---|---|---|
| Formulation | A | B | C |
| N-desmethylzolpidem | 50.0 | 100.0 | 200.0 |
| Lactose | 48.5 | 148.5 | 48.5 |
| Titanium Dioxide | 0.5 | 0.5 | 0.5 |
| Magnesium Stearate | 1.0 | 1.0 | 1.0 |
| Fill Weight | 100.0 | 250.0 | 250.0 |

The active ingredient (i.e., N-desmethylzolpidem) is sieved and blended with the excipients. The mixture is filled into suitably sized two-piece hard gelatin capsules using suitable machinery. Other doses may be prepared by altering the ratio of N-desmethylzolpidem and pharmaceutically acceptable carrier, the fill weight and, if necessary, by changing the capsule size to suit.

5.4. Example 4: Oral Formulation

Hard gelatin capsules of N-desmethylzolpidem may be made using the ingredients provided in Table 4:

TABLE 4

| | Hard Gelatin Capsule Unit Dosage Forms | | |
|---|---|---|---|
| Component | 2.5 mg capsule (amount in mg) | 5 mg capsule (amount in mg) | 20 mg capsule (amount in mg) |
| N-desmethylzolpidem | 2.5 | 5.0 | 20.0 |
| Microcrystalline Cellulose | 90.0 | 90.0 | 90.0 |
| Pre-gelatinized Starch | 100.3 | 97.8 | 82.8 |

TABLE 4-continued

Hard Gelatin Capsule Unit Dosage Forms

| Component | 2.5 mg capsule (amount in mg) | 5 mg capsule (amount in mg) | 20 mg capsule (amount in mg) |
|---|---|---|---|
| Croscarmellose | 7.0 | 7.0 | 7.0 |
| Magnesium Stearate | 0.2 | 0.2 | 0.2 |

The active ingredient is sieved and blended with the excipients listed. The mixture is filled into suitably sized two-piece hard gelatin capsules using suitable machinery and methods well known in the art. See Remington's Pharmaceutical Sciences, 16th or 18th Editions, each incorporated herein in its entirety by reference thereto. Other doses may be prepared by altering the fill weight and, if necessary, changing the capsule size to suit. Any of the stable, non-lactose hard gelatin capsule formulations above may be formed.

5.5. Example 5: Oral Formulation

Compressed tablet formulations of N-desmethylzolpidem may be made using the ingredients provided in Table 5:

TABLE 5

Compressed Tablet Formulations

| Component | 2.5 mg tablet (amount in mg) | 5 mg tablet (amount in mg) | 20 mg tablet (amount in mg) |
|---|---|---|---|
| N-desmethylzolpidem | 2.5 | 5.0 | 20.0 |
| Microcrystalline Cellulose | 90.0 | 90.0 | 90.0 |
| Pregelatinized Starch | 100.3 | 97.8 | 82.8 |
| Croscarmellose | 7.0 | 7.0 | 7.0 |
| Magnesium Stearate | 0.2 | 0.2 | 0.2 |

The active ingredient is sieved through a suitable sieve and blended with the non-lactose excipients until a uniform blend is formed. The dry blend is screened and blended with the magnesium stearate. The resulting powder blend is then compressed into tablets of desired shape and size. Tablets of other strengths may be prepared by altering the ratio of the active ingredient (ie., N-desmethylzolpidem) to the excipient(s) or modifying the tablet weight.

The embodiments of the invention described above are intended to be merely exemplary, and those skilled in the art will recognize, or be able to ascertain using no more than routine experimentation, numerous equivalents to the specific procedures described herein. All such equivalents are considered to be within the scope of the invention and are encompassed by the following claims.

What is claimed is:

1. A method of treating or preventing a disease or condition in a patient which is affected by the modulation of one or more central or peripheral benzodiazepine receptors, which comprises administering to a patient in need of such treatment or prevention a therapeutically effective amount of N-desmethylzolpidem, or a pharmaceutically acceptable salt, solvate, or clathrate thereof.

2. The method of claim 1 wherein the disease or condition is a sleep disorder.

3. The method of claim 2 wherein the sleep disorder is insomnia.

4. The method of claim 1 wherein the disease or condition is an affective disorder.

5. The method of claim 4 wherein the affective disorder is depression.

6. The method of claim 4 wherein the affective disorder is attention deficit disorder or attention deficit disorder with hyperactivity.

7. The method of claim 1 wherein the disease or condition is a convulsive state.

8. The method of claim 7 wherein the convulsive state is epilepsy.

9. The method of claim 1 wherein the disease or condition is anxiety.

10. The method of claim 9 wherein the anxiety is acute anxiety.

11. The method of claim 9 wherein the anxiety is chronic anxiety.

12. The method of claim 1 wherein the disease or condition is aggressive behavior.

13. The method of claim 1 wherein the disease or condition is spasticity or acute muscle spasm.

14. The method of claim 1 wherein the disease or condition is a behavioral disorder.

15. The method of claim 1 wherein the disease or condition is a schizophrenic disorder.

16. The method of claim 1 wherein the disease or condition is associated with abnormal plasma hormone levels.

17. The method of claim 16 wherein the disease or condition is an endocrine disorder.

18. The method of claim 1 wherein the patient is human.

19. The method of claim 1 wherein the therapeutically effective amount of N-desmethylzolpidem or pharmaceutically acceptable salt, solvate, or clathrate thereof is from about 1 mg to about 500 mg.

20. The method of claim 19 wherein the therapeutically effective amount of N-desmethylzolpidem or pharmaceutically acceptable salt, solvate, or clathrate thereof is from about 5 mg to about 250 mg.

21. The method of claim 20 wherein the therapeutically effective amount of N-desmethylzolpidem or pharmaceutically acceptable salt, solvate, or clathrate thereof is from about 10 mg to about 200 mg.

22. A pharmaceutical composition comprising N-desmethylzolpidem, or a pharmaceutically acceptable salt, solvate, or clathrate thereof.

23. The pharmaceutical composition of claim 22 wherein said pharmaceutical composition further comprises a pharmaceutically acceptable carrier.

24. The pharmaceutical composition of claim 22 wherein said pharmaceutical composition is suitable for parenteral, oral, topical, transdermal, or mucosal administration to a patient.

25. The pharmaceutical composition of claim 24 wherein said pharmaceutical composition is suitable for oral administration to a patient.

26. An individual dosage form of N-desmethylzolpidem which comprises N-desmethylzolpidem, or a pharmaceutically acceptable salt, solvate, or clathrate thereof.

27. The dosage form of claim 26 wherein said dosage form further comprises a pharmaceutically acceptable carrier.

28. The dosage form of claim 27 wherein said dosage form is a tablet, caplet, or capsule.

29. The dosage form of claim 26 wherein said dosage form comprises from about 1 mg to about 500 mg of N-desmethylzolpidem or a pharmaceutically acceptable salt, solvate, or clathrate thereof.

30. The dosage form of claim 29 wherein said dosage form comprises from about 5 mg to about 250 mg of N-desmethylzolpidem or a pharmaceutically acceptable salt, solvate, or clathrate thereof.

31. The dosage form of claim 30 wherein said dosage form comprises from about 10 mg to about 150 mg of N-desmethylzolpidem or a pharmaceutically acceptable salt, solvate, or clathrate thereof.

* * * * *